United States Patent [19]
Rossiter

[11] Patent Number: 4,822,166
[45] Date of Patent: * Apr. 18, 1989

[54] FLOW-THROUGH CELLS FOR SPECTROSCOPY

[76] Inventor: Valentine J. Rossiter, 16 Rathmore Ave., Kilmacud, Stillorgan, Dublin, Ireland

[*] Notice: The portion of the term of this patent subsequent to Jan. 18, 2004 has been disclaimed.

[21] Appl. No.: 134,555

[22] Filed: Dec. 16, 1987

Related U.S. Application Data

[63] Continuation of Ser. No. 807,219, Dec. 12, 1985, which is a continuation-in-part of Ser. No. 729,076, Apr. 30, 1985, abandoned, which is a continuation of Ser. No. 419,275, Sep. 17, 1982, abandoned.

[51] Int. Cl.$^4$ ............................................. G01N 21/05
[52] U.S. Cl. ..................................... 356/246; 356/244; 250/343
[58] Field of Search ................ 356/244, 246; 250/343, 250/428

[56] References Cited

U.S. PATENT DOCUMENTS

| | | | |
|---|---|---|---|
| 3,307,447 | 12/1980 | Carleton et al. | 356/246 |
| 3,583,817 | 6/1971 | Rachlis et al. | 356/410 |
| 3,614,452 | 1/1969 | Felton | 356/246 |
| 3,684,386 | 8/1972 | Noll | 356/246 |
| 3,795,450 | 3/1984 | Munk | 356/246 |
| 4,019,372 | 4/1977 | Parkell et al. | 356/410 |
| 4,181,437 | 1/1980 | Rossiter | 356/246 |
| 4,192,614 | 3/1980 | deMey, II et al. | 356/410 |
| 4,374,620 | 2/1983 | Berick et al. | 356/246 |
| 4,440,013 | 4/1984 | Adams | 356/410 |

FOREIGN PATENT DOCUMENTS

| | | | |
|---|---|---|---|
| 2032150 | 1/1972 | Fed. Rep. of Germany | 356/244 |
| 56-147024 | 11/1981 | Japan | 356/244 |

OTHER PUBLICATIONS

Waggener et al., "Reliable Optical Window for Cells Subjected to Widely Cycling Temperatures & Pressures", Rev. of Sci. Inst. vol. 30 #8, Aug. 1959, pp. 677–679.

Primary Examiner—Vincent P. McGraw
Attorney, Agent, or Firm—Sughrue, Mion, Zinn, Macpeak, and Seas

[57] ABSTRACT

A flow-through cell for spectroscopy has very small dead-volume and is designed for minimal mixing. Windows at each end of the optical cell formed in a massive block are swept by the true flow, with outlets and inlets into the cell being tortuous and having at least a part parallel to and defined by the window. The windows may be held in the block by angular screw means engaged in blocks which are of a different material from that of the rings. The body of the optical cavity is between 0.4 mm and 6 mm in diameter and has a length between 1 cm and 15 cm to be traversed by an analyzing beam. The operating range is typically from between 20° and 270° C. and over a pressure range of from between vacuum and 2000 PSIG.

10 Claims, 3 Drawing Sheets

FLOW-THROUGH CELLS FOR SPECTROSCOPY

CROSS REFERENCE

This application is a continuation of Ser. No. 807,219 filed Dec. 12, 1985 which is a continuation-in-part application of application Serial No. 729,076 filed Apr. 30, 1985 now abandoned, which application is a continuation of application Ser. No. 419,275, filed Sept. 17, 1982, now abandoned. The contents of these abandoned applications are made a part hereof by reference, and the benefit of these applications under 35 USC 120 is claimed.

BACKGROUND OF THE INVENTION

1. Field of the Invention

This invention pertains to cells for samples of gases, vapours and/or super critical fluids to be examined spectroscopically.

2. Background of the Prior Art

The prior art discloses detector cells used in chromatography and are primarily concerned with liquid chromatography. Representative of the prior art are listed on the attached form and copies are attached for the record.

Berick et al. (U.S. Pat. No. 4,374,620) is a photometric flow cell for liquid chromatography which employs a porous frit to give turbulent flow to liquid flowing through the cell at high pressure.

Adams (U.S. Pat. No. 4,440,013) relates to a gas chromatograph having a flexible capillary column therein for separating components of a sample.

Rossiter (U.S. Pat. No. 4,181,437) is directed to a spectral analysis cell for the batch spectroscopic analysis of materials.

deMey, II et al. (U.S. Pat. No. 4,192,614) is a spectrophotometer detector cell for use with liquid chromatography.

Munk (U.S. Pat. No. 3,795,450) is directed to a photometry detector assembly having a sample cell and reference cell for use in a dual beam optical absorption photometry instrument.

Felton (U.S. Pat. No. 3,614,452) is directed to a method of making photometric measurements of flowing fluids wherein a fluid stream is split into two substantially equal component streams which are directed in opposite directions.

Carleton et al (U.S. Pat. No. 3,307,447) is directed to an apparatus for optically analyzing material and employs a relatively long fluid path for analysis.

SUMMARY OF THE INVENTION

Unlike the prior art devices and methods, this invention is particularly concerned with flow-through cells and especially with cells designed to provide good flow characteristics, low "dead-volume" and usable in an on-line, flow-through mode so that there is minimal mixing of material as it passes through the cell. Such a cell is particularly suited to the spectroscopic examination of materials eluting from chromatographs or other systems providing samples with time varying composition.

Further, this invention describes cells having various novel features in which the invention resides. For example, some of these features are applicable in cells of other types, and notably a cell window mounting system herein can be used for a static cell.

Another aspect of this invention is broadly concerned with providing a flow-through cell which can be accommodated in the sample compartment of a spectrophotometer. For this, it is desirable that the cell should have a length of not more than 20 cm, and possibly not more than 11 cm. The internal diameter of the light pipe within the cell will preferably be not substantially more than 8 mm, possibly not substantially more than 6 mm. Cells as described hereinafter can be used with standard sampling equipment and afford the possibility of tailoring the cell to a particular chromatographic application.

Yet another aspect of the invention is concerned with a manner of mounting windows at the ends of the light pipe of the cell. The windows are held in cavities at the ends of the cell and are held in place by screws with axial apertures through which the spectrophotometer beam passes.

And still another aspect of the invention is to provide a cell body having an optical cavity between 0.4 mm to 6 mm in diameter and between 1 cm and 15 cm in length to be traversed by an analyzing beam.

These and other objects of the invention will become apparent to those skilled in the art to which the invention pertains from a reading of the following specification when taken in light of the annexed drawings.

DESCRIPTION OF THE PREFERRED EMBODIMENT OF THE INVENTION

Figure 1:
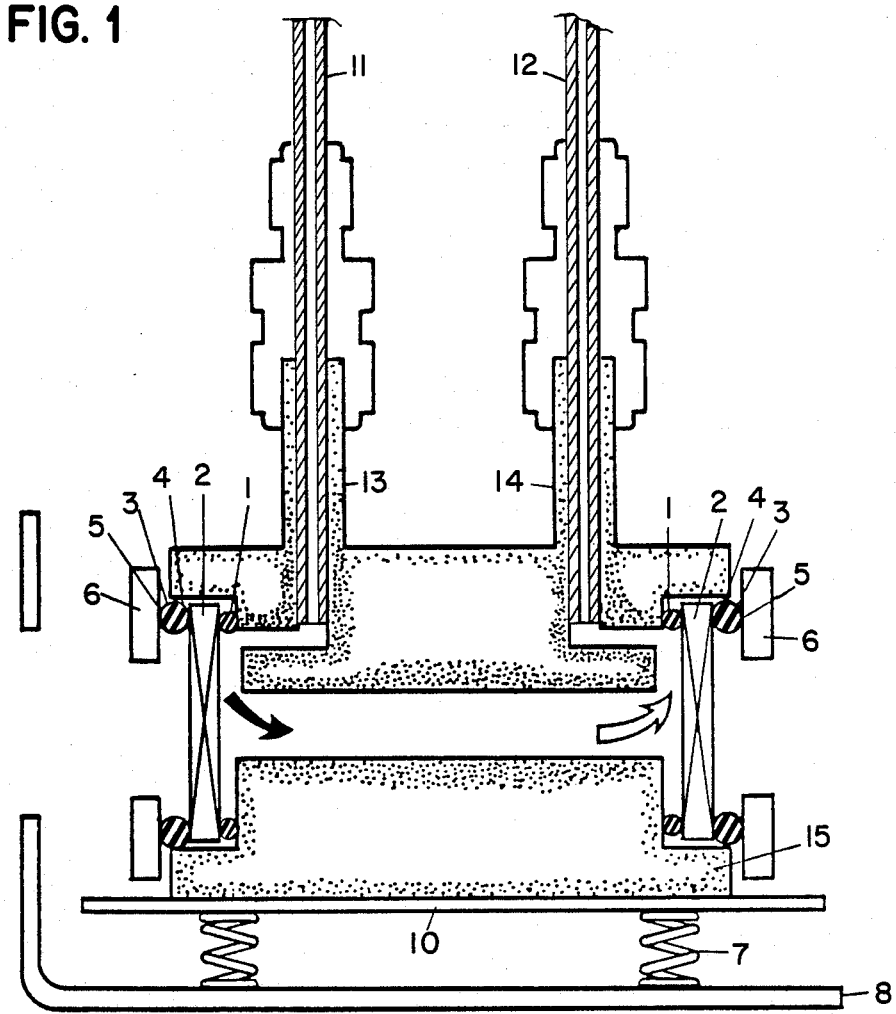
FIG. 1 is a perspective view in section of the invention.
Figure 2:
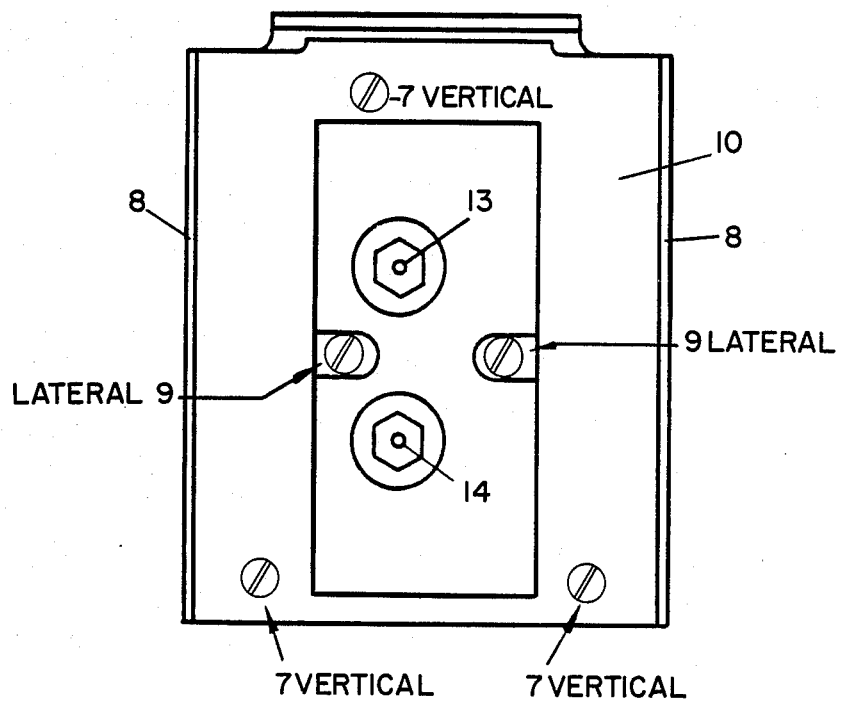
FIG. 2 is a plan view of the mounting assembly.

Referring to the structure of FIG. 1, there is shown a flow-through cell which can be advantageously used with Fast Fourier Transform infrared Spectrophotometers to examine materials eluting from gas chromatographs. Typical dimensions of the light-pipe cell cavity are L=6 cm and internal diameter D in the range of 0.4 mm to 6 mm. This cell can be heated to at least 270° C. over a pressure range from vacuum to at least 15 PSIG. The cell can also operate from up to 200° C. over a pressure range from vacuum to at least 2000 PSIG. The gas can enter either at 13 or 14 (the design of the pipe is symmetrical). Note that ports 13 and 14 can be fabricated so that they are integral with the cell body 15. This eliminates unnecessary joints in the system. Also, inlet and outlet connection tubes 11 and 12 typically 1/16 inch tube can be brought into the cell through ports 13 and 14 using conventional (drilled through) tube unions, so avoiding dead-volume and improving heat transfer from the cell to the connections. The window mounting system shown in FIG. 1 is that described in U.K. Pat. No. 1,576,932. This arrangement allows the cell to be heated to at least 270° C. while maintaining a sufficiently good gas tight seal on the delicate infrared transmitting windows (2) (typically polished potassium bromide crystals). In FIG. 1, there is shown an inner gasket 1 (typically Poly Tetra Fluoro Ethylene, PTFE) and an outer gasket 3 (typically silicone rubber). Item number 6 denotes a clamp plate for the window and gasket assembly. The device can be mounted, via plate 10, spring 7, bracket 8 so that it fits the standard sample compartment of a spectrophotometer; optical adjustment is provided within the overall mounting system as illustrated in FIG. 2 and additional optics are not generally required.

Figure 3:
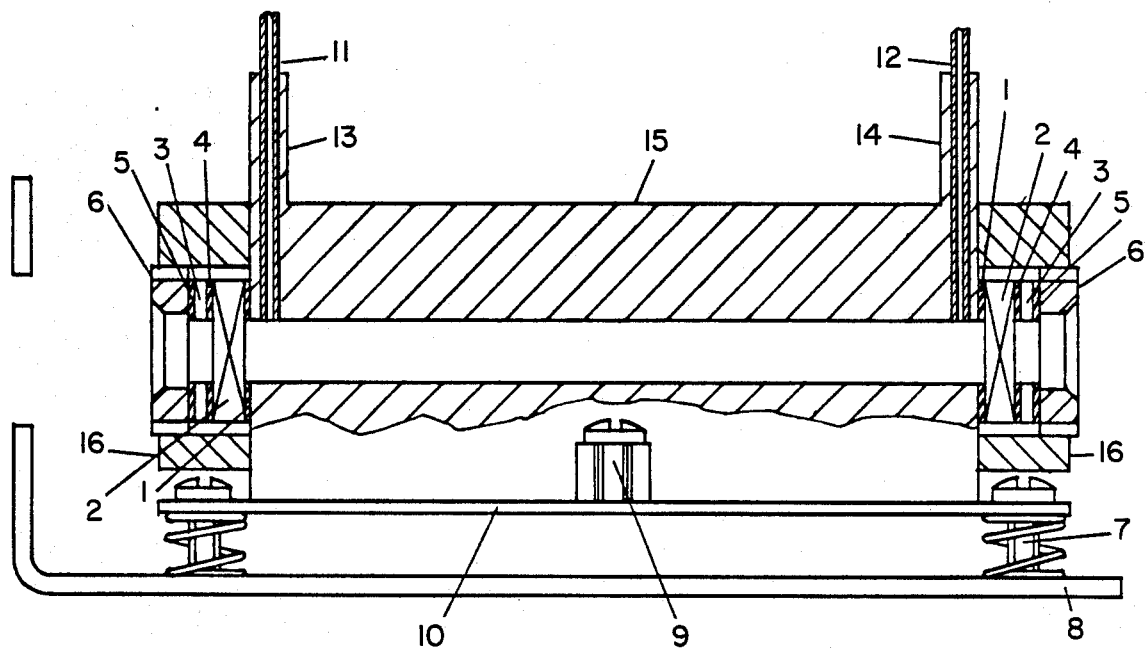
FIG. 3 is a perspective view in section showing a modified form of the assembly bracket.

FIG. 3 illustrates another design of a high temperature, low-volume, light-pipe cell for the spectroscopic examination of vapours. While the design illustrated in FIG. 1 is widely useful, it is not readily fabricated in a chemically inert format. Certain materials easily undergo chemical breakdown when exposed in the vapour state to mildly reactive surfaces at high temperatures. The use of glass linings and gold coatings are advantageous in such circumstances, but the sharp angles within narrow bores (as illustrated in FIG. 1) does not lend themselves to such solutions. This problem is overcome by the invention illustrated in FIG. 3. Here the inlet and outlet tubes 11 and 12 (which may be narrow bore quartz, glass, glasslined metal or other inert materials) are brought directly to either end of the light-pipe and through the entrance and exits ports 13 and 14; these ports 13 and 14 can be fabricated as an integral part of the cell body 15 so that there are no joints within the cell structure. The inner bore of the light-pipe can be coated with gold (or other suitable material) by conventional means. Consequently, the sample material passing through the cell need contact only inert surfaces. A new window clamping system is employed which is more convenient in practice and equally effective as that illustrated in FIG. 1. The windows 2 are circular and are retained within clamp block 16 which is bolted to the cell body 15. The clamp block 16 is internally threaded to take hollow screw 6. The window then seals against the cell body 15 through a soft inner gasket 1 (typically PTFE) and is retained by screw 6 through an exterior gasket system 3, 4 and 5. Item 3 denotes a compression gasket (typically silicone rubber) and 4 and 5 are slip gaskets (typically PTFE). It has been found to be advantageous to fabricate 16 and 6 in dissimilar metals (typically 16 in aluminium and 6 in steel). The cell can be mounted (via screw 9, plate 10, spring and screw assembly 7, mounting plate 8) in a manner generally similar to that previously described and illustrated in FIG. 3. Other methods of fabrication include making 16 integral with cell body 15.

The conventional method of interfacing Fast Fourier Transform Infrared Sepctrophotometers to gas chromatographs is to use a special long light-pipe (typically 40 cm×3 mm internal diameter, gold coated glass) mounted in an additional optical bench into which the gas chromatograph is plumbed. Such systems are expensive, space consuming and may involve "dedicating" the instrument to that application to an inconvenient extent. The device described in FIG. 3 (with mounting system shown in FIG. 2) can be mounted directly within the normal sample space of the spectrophotometer. Optical adjustment is easily provided within the mounting system and additional optics are not generally necessary. By virtue of the smaller volume of such a cell, the cell more closely matches the requirements of the chromatography. For example, with a 2 mm i.d. pipe, the volume is suited to "capillary" gas chromatography. The sensitivity which can be achieved with such a short pipe is not necessarily lower than that offered by conventional longer pipes; this is particularly the case with lower quantities of materials eluting in small volumes of carrier gas from the chromatograph. The lack of dead volume together with the inherently low volumes of such cells means that peak broadening and/or mixing within the light-pipe is not a significant problem and so the separation performance of the chromatograph is better maintained by such cells.

The design of these cells is such that, by means of a high temperature, low volume venting valve placed between the gas chromatograph and the cell, the flow through cell can be interupted by opening the vent valve so leaving a particular sample component isolated in the cell while the gas chromatograph effluent is vented by the valve. This allows greater scanning time for that component so improving the signal to noise ratio of the spectrum by repeated scanning of the sample. The "trapped" material diffuses only slowly from the cell by reason of the relatively restricted entrance and exit passages; this can, of course, be further reduced by conventional means of isolating the sample in the cell with blanking arrangements or further valving. In completion of the necessary further scans, flow is resumed on closing the vent valve.

Whereas such cells are particularly suited to the needs of Fast Fourier Transform Infrared Spectrophotometers, they can with advantage be applied to other types of spectrophotometer, for example, dispersive infrared instruments.

Figure 4:
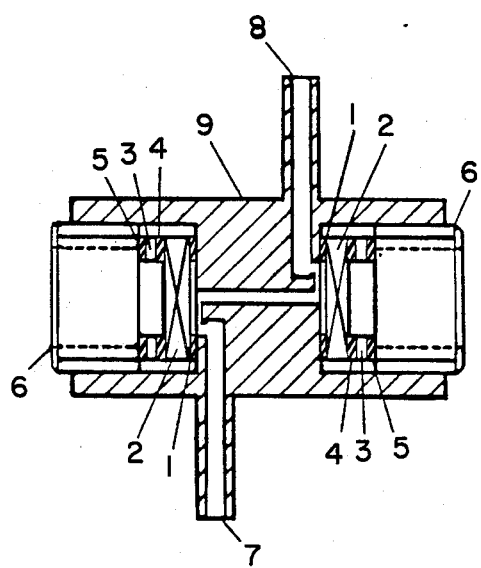
FIG. 4 is a perspective view in section of a modified form of the invention as shown in FIG. 1.

FIG. 4 illustrates a flow-through cell designed for the analysis of super-critical fluid samples by spectroscopy. One application of such a cell is the analysis of material eluting from a super-critical fluid chromatograph by means of ultraviolet/infrared and/or visible radiation. The length of the light-pipe cavity is typically 1 cm and the diameter is typically 1.5 mm. The entrance and exits ports 7 and 8 can be fabricated as integral parts of the cell body 9. The flow through the cell is arranged so that the material enters at one window 2 and leaves at the opposite window 2. The cell is symmetrical and the flow ca be in either direction. The inlet and outlet connection pipes (typically 1/16 inch o.d. stainless steel tubing) can be brought through drilled-through conventional pipe unions so that they are inserted into the body of the cell to eliminate undesirable dead-volume. The windows 2 (typically quartz) are sealed through a soft inner gasket 1 (typically PTFE) using a composite external gasket 3, 4, 5 for compression of a hollow compression screw 6. The cell can be mounted on an appropriately designed adjustable mounting system to provide easy alignment in the spectrophotometer.

Cells of this design have been found to be very effective when used with conventional spectrophotometers for the analysis of samples eluting from super-critical fluid chromatographs. The cells show excellent flow characteristics and the sensitivity and selectivity of the spectrophotometer can be advantageously exploited. Generally, materials are not so prone to chemical breakdown in contact with metal surfaces while in the supercritical state and so such cells can be fabricated from appropriate metals, for example 316 grade stainless steel. Bringing the inlet and outlet connection pipes close to but not directly into, the optical cavity is therefore a generally satisfactory method of achieving the design objectives. However, if it should be desired to make the system more inert, then the methods illustrated in the cell design shown in FIG. 3 could similarly be applied to this case While the invention has been described with regard to a specific embodiment thereof, it will be appreciated by those skilled in the art to which this invention pertains that various changes may be made in the invention without departing from the spirit and scope thereof.

What I claim is:

1. A flow-through optical cell for infrared spectroscopy of gas of time-varying composition and eluting from a chromatograph, comprising:
   a body having an optical cavity between 0.4 mm to 6 mm in diameter and between 1 cm and 15 cm in length to be traversed by an analyzing beam;
   a gas inlet being a raised port integral with said body and having a bore communicating with the optical cavity adjacent one end of the cavity;
   a gas outlet being a raised port integral with said body and having a bore communicating with the optical cavity adjacent the opposite end of the cavity; and
   an infrared radiation-transmitting window at or adjacent each end of the optical cavity, a gas-sealing gasket between the window and the body, and at least one gas-sealing gasket on the opposite side of the window;
   an operating range of said cell being from between 20° C. and 270° C. and over a pressure range from between vacuum and 15 PSIG.

2. A flow-through cell for spectroscopy according to claim 1, wherein:
   at least one end of the cell inlet or outlet is arranged to cause flow over the surface of the respective windows.

3. A flow-through cell for spectroscopy according to claim 2, wherein:
   each window is retained to the body by means of a screw ring through the aperture of which the analyzing beam can press to or from the respective windows.

4. A flow-through cell for spectroscopy according to claim 3, wherein:
   said screw ring is engaged in metal block separate from but secured to the body of the cell.

5. A flow-through cell for spectroscopy according to claim 4, wherein:
   said screw ring is made of a metal different from that of the block.

6. A flow-through optical cell for infrared spectroscopy of gas of time-varying and eluting from a chromatograph, comprising:
   a body having an optical cavity between 0.4 to 6 mm in diameter and between 1 cm and 15 cm in length to be traversed by an analyzing beam;
   a gas inlet being a raised port integral with said body and having a bore communicating with the optical cavity adjacent one end of the cavity;
   a gas outlet being a raised port integral with said body and having a bore communicating with the optical cavity adjacent the opposite end of the cavity; and
   an infrared radiation-transmitting window at or adjacent each end of the optical cavity, a gas-sealing gasket between said window and said body, and at least one gas-sealing gasket on the opposite side of the window;
   an operating range of said cell being from between 20° C. and 270° C. and over a pressure range from between vacuum and 15 PSIG; and
   said body being a single integral mass.

7. A flow-through optical cell for infrared spectroscopy of gas of time-varying composition and eluting from a chromatograph, comprising:
   a body having an optical cavity between 0.4 cm to 6 mm in diameter and between 1 cm and 15 cm in length to be traversed by an analyzing beam;
   a gas inlet communicating with the optical cavity at or adjacent one end of the cavity;
   a gas outlet communicating with the optical cavity at or adjacent the opposite end of the cavity;
   an infrared radiation-transmitting window at or adjacent each end of the optical cavity;
   an operating range of said cell being from between 20° C. and 270° C. and over a pressure range from between vacuum and 15 PSIG; and
   mounting bracket-and-spring means, attached to the body, for mounting the cell to the standard compartment of a spectrophotometer.

8. A flow-through cell as defined in claim 1, 2, 5, 6 or 7 wherein each window is made of polished potassium bromide crystals.

9. A flow-through cell as defined in claim 1, wherein said length is 5 cm.

10. A flow-through optical cell for real-time spectroscopy of hot vapors of time-varying composition and eluting from a gas chromatograph, comprising:
    a body having an optical cavity between 0.4 mm to 6 mm in diameter and between 1 cm and 15 cm in length to be traversed by an analyzing beam;
    a gas inlet in the form of a raised port integral with said body and having a bore communicating with the optical cavity adjacent one end of the cavity;
    a gas outlet in the form of a raised port integral with said body and having a bore communicating with the optical cavity adjacent the opposite end of the cavity; and
    an analyzing beam radiation-transmitting window at or adjacent each end of the optical cavity, a gas-sealing gasket between the window and the body, and at least one gas-sealing gasket on the opposite side of the window;
    an operating range of said cell being from either between 20° C. and 270° C. and over a pressure range from between vacuum and 15 PSIG or between 20° C. and 200° C. over a pressure range from between vacuum and 2,000 PSIG.

* * * * *